United States Patent [19]
Chun et al.

[11] Patent Number: 6,063,912
[45] Date of Patent: May 16, 2000

[54] PLACENTA TROPHOBLAST-SPECIFIC GENE

[75] Inventors: Jong-Yoon Chun; Yun-Jeong Han, both of Kwangju, Rep. of Korea

[73] Assignee: Korea Kumho Petrochemical Co., Ltd., Seoul, Rep. of Korea

[21] Appl. No.: 09/129,888

[22] Filed: Aug. 6, 1998

[51] Int. Cl.[7] .................................................. C07H 21/04
[52] U.S. Cl. ............................ 536/23.1; 536/23.5; 435/6; 435/69.1; 435/252.3; 435/320.1; 436/504
[58] Field of Search .................................. 536/23.1, 23.5; 435/6, 69.1, 252.3, 320.1; 436/504

[56] References Cited

PUBLICATIONS

Han et al. (Mar. 3, 1998) "Psx, a Novel Murine Homeobox Gene Expressed in Placenta" Gene 207, pp. 159–166.
Maniatis et al. (1982) Molecular Cloning A Laboratory Manual. Cold Spring Harbor Laboratory, pp. 122–123.
Han et al. (Mar. 19, 1998) Direct Submission, EMBL/GenBank Database, Accession No. AF017453.
Marra et al. (Jul. 8, 1998) The WashU–HHMI Mouse EST Project, EMBL/GenBank/EST Database, Accession No. AI047063.
Kurman, et al., *Placenta*, 5(1984), pp. 349–370.
Guillemot, et al., *Nature*, 371(Sep. 22, 1994), pp. 333–336.
El–Refaey, et al., *Human Reproduction*, 10:2(1995), pp. 475–478.
Cross, et al., *Science*, 266:2(Dec. 1994), pp. 1508–1518.
Lösch, et al., *Acta Obstet Gynecol Scand*, 75(1996), pp. 753–756.
Shih, et al., *Verh. Dtsch. Ges. Path.*, 81(1997), pp. 266–272.
Gehring et al., *Annu. Rev. Biochem.*, 63(1994), pp. 487–526.
Cadepond et al., *Annu Rev. Med.*, 48(1997), pp. 129–156.
Rossant, *Developmental Biology*, 6(1995), pp. 237–247.
Sapin et al., *Developmental Biology*, 191(1997), pp. 29–41.
Orwig, et al., *Trophoblast Research*, 11(1998), pp. 65–85.

*Primary Examiner*—Bradley Sisson
*Assistant Examiner*—Enrique D. Longton
*Attorney, Agent, or Firm*—Kenyon & Kenyon

[57] ABSTRACT

Expression of the polynucleotide molecule, Psx, is restricted to placenta, and in particular, to placenta trophoblast cell layers during embryogenesis. The expression pattern of Psx is exploited to detect trophoblast specific lineages, such as labyrinthine trophoblast layer and giant cells. The invention provides an isolated DNA molecule encoding Psx protein, and chimeric constructs, vector and host cells containing the isolated DNA. Also provided is a method for identifying putative abortion-inducing agents, which may offer an alternative to surgical abortion.

6 Claims, 11 Drawing Sheets

```
GGAAGCCTCTTCGGGAGCAGCGTCGGATCCAGAGATTCTCGCTATGGAAACTCCTCAAGA      60
                                          M   E   T   P   Q   D    6

CAGCCGCCAAAGCATCCAAAAGCCTCCGAGTCCGGCAGCCGAGGAGGACAAGGAAGAACA     120
  S   R   Q   S   I   Q   K   P   P   S   P   A   A   E   E   D   K   E   E   Q    26

GCCTGGTGGGAATGCAGTGGTCTCCGGGGCTCCAGAGGAAAGAATAGACAAGAAAGAGCT     180
  P   G   G   N   A   V   V   S   G   A   P   E   E   R   I   D   K   K   E   L    46

TGTACTGAACTGGCTCGCTCAGGGTGAGTTTGATCAGGGCGAAGGCCTCAGGGCGAGGTT     240
  V   L   N   W   L   A   Q   G   E   F   D   Q   G   E   G   L   R   A   R   L    66

GCTGGAGGTGAGCAGGCTCAAGAAGAGCCTGTCCATTGAGTCCAGCTCAGGAAGCCACTG     300
  L   E   V   S   R   L   K   K   S   L   S   I   E   S   S   S   G   S   H   W    86

GAGGAGAAGAGGAGGGAGAAAAAAGGAAGGAGAAATGGAAGGAAGACATGCTGGTGATGG     360
  R   R   R   G   G   R   K   K   E   G   E   M   E   G   R   H   A   G   D   G   106

TGCTTCTAGCTCCGAGGATGACAGCATCCTGGAAGAAGGCGGCCAAAACATAGATCAACA     420
  A   S   S   S   E   D   D   S   I   L   E   E   G   G   Q   N   I   D   Q   Q   126

GCCGCCTCAGCAAGAGGCAGCCAGTCCTGATAGCATCAGAAACCCACATGTTCTGAATAG     480
  P   P   Q   Q   E   A   A   S   P   D   S   I   R   N   P   H   V   L   N   R   146

GCTGGCTCAACTGCGGTACAGACGCACCAGGTTCACCCACTCTCAGCTGCATGACCTGGA     540
  L   A   Q   L   R   Y   R   R   T   R   F   T   H   S   Q   L   H   D   L   E   166

GCGCCTTTTCCAAGAGACTCGCTACCCCAGCTTGCGAGCAAGGAGGGATCTTGCACGATG     600
  R   L   F   Q   E   T   R   Y   P   S   L   R   A   R   R   D   L   A   R   W   186

GATGGGTGTGGATGAATGTGATGTGCAGAATTGGTTTCGGATGAGGAGAGCCCTTTTCCA     660
  M   G   V   D   E   C   D   V   Q   N   W   F   R   M   R   R   A   L   F   Q   206

GAGAAACAGGAGAGTGCTGATGTTCTGCGAACTGCCGCCTCTTCCCCAGAGCGACTCTCC     720
  R   N   R   R   V   L   M   F   C   E   L   P   P   L   P   Q   S   D   S   P   226

TGAAGATTTTGGAGCAGACTTGAGTGCCAGCCCTGTCATGGAGCCAGATGAGGATGGCTT     780
  E   D   F   G   A   D   L   S   A   S   P   V   M   E   P   D   E   D   G   F   246

CTTCTGAGCCACCCATGATGGCCATGACAACCTTTTCTTCTCTACAATTATTTCAGCAAT     840
  F   *                                                                            247

AAAGATGAGCATTCTGAATAAAAAAAAAAAAAAAAAAA                                             877
```

FIG. 1

```
GGAAGCCTCTTCGGGAGCAGCGTCGGATCCAGAGATTCTCGCTATGGAAACTCCTCAAGA      60
                                             M  E  T  P  Q  D      6

CAGCCGCCAAAGCATCCAAAAGCCTCCGAGTCCGGCAGCCGAGGAGGACAAGGAAGAACA     120
 S  R  Q  S  I  Q  K  P  P  S  P  A  A  E  E  D  K  E  E  Q      26

GCCTGGTGGGAATGCAGTGGTCTCCGGGGCTCCAGAGGAAAGAATAGACAAGAAAGAGCT     180
 P  G  G  N  A  V  V  S  G  A  P  E  E  R  I  D  K  K  E  L      46

TGTACTGAACTGGCTCGCTCAGGGTGAGTTTGATCAGGGCGAAGGCCTCAGGGCGAGGTT     240
 V  L  N  W  L  A  Q  G  E  F  D  Q  G  E  G  L  R  A  R  L      66

GCTGGAGGTGAGCAGGCTCAAGAAGAGCCTGTCCATTGAGTCCAGCTCAGGAAGCCACTG     300
 L  E  V  S  R  L  K  K  S  L  S  I  E  S  S  S  G  S  H  W      86

GAGGAGAAGAGGAGGGAGAAAAAAGGAAGGAGAAATGGAAGGAAGACATGCTGGTGATGG     360
 R  R  R  G  G  R  K  K  E  G  E  M  E  G  R  H  A  G  D  G     106

TGCTTCTAGCTCCGAGGATGACAGCATCCTGGAAGAAGGCGGCCAAAACATAGATCAACA     420
 A  S  S  S  E  D  D  S  I  L  E  E  G  G  Q  N  I  D  Q  Q     126

GCCGCCTCAGCAAGAGGCAGCCAGTCCTGATAGCATCAGAAACCCACATGTTCTGAATAG     480
 P  P  Q  Q  E  A  A  S  P  D  S  I  R  N  P  H  V  L  N  R     146

GCTGGCTCAACTGCGGTACAGACGCACCAGGTTCACCCACTCTCAGCTGCATGACCTGGA     540
 L  A  Q  L  R  Y  R  R  T  R  F  T  H  S  Q  L  H  D  L  E     166

GCGCCTTTTCCAAGAGACTCGCTACCCCAGCTTGCGAGCAAGGAGGGATCTTGCACGATG     600
 R  L  F  Q  E  T  R  Y  P  S  L  R  A  R  R  D  L  A  R  W     186

GATGGGTGTGGATGAATGTGATGTGCAGAATTGGTTTCGGATGAGGAGAGCCCTTTTCCA     660
 M  G  V  D  E  C  D  V  Q  N  W  F  R  M  R  R  A  L  F  Q     206

GAGAAACAGGAGAGTGCTGATGTTCTGCGAACTGCCGCCTCTTCCCCAGAGCGACTCTCC     720
 R  N  R  R  V  L  M  F  C  E  L  P  P  L  P  Q  S  D  S  P     226

TGAAGATTTTGGAGCAGACTTGAGTGCCAGCCCTGTCATGGAGCCAGATGAGGATGGCTT     780
 E  D  F  G  A  D  L  S  A  S  P  V  M  E  P  D  E  D  G  F     246

CTTCTGAGCCACCCATGATGGCCATGACAACCTTTTCTTCTACAATTATTTCAGCAAT      840
 F  *                                                            247

AAAGATGAGCATTCTGAATAAAAAAAAAAAAAAAAAA                            877
```

FIG. 2

|  | HELIX1 | HELIX2 | HELIX3 | Identity(%) |
|---|---|---|---|---|
| Psx | LRYRRTRFTH SQLHDLERLF | QETRYPSLRA RRDLARWMGV | DECDVQNWFR MRRALFQRNR | 100 |
| Mhox | Q-RN--T-NS ---QA----V- | ER-H---DAFV -E-----RVNL | T-AR---V--Q N---K-R--E | 50 |
| S8 | Q-RN--T-NS ---QA----V- | ER-H---DAFV -EE----RVNL | S-AR---V--Q N---K-R--E | 48 |
| Smox-3 | Q-RI--T--S L--KE----A- | ----H---DIYT -E----LRIDL | T-AR---V--Q N---K-RKTE | 48 |
| GSC | K-RH--I-TD E--EA--N--- | ----K---DVGT -EQ---KVHL | R-EK-EV---K N---KWR-QK | 47 |
| Phox2 | Q-RI--T--S A--KE----V- | A--H---DIYT -EE--LKIDL | T-AR---V--Q N---K-RKQE | 45 |
| Shox | Q-RS--N--L E---NE------ | D--H---DAFM -EE--SQRL-L | S-AR---V--Q N---KCRKQE | 45 |
| Rx | H-RN--T--T Y---E----A- | EKSH---DVYS -EE---MKVNL | P-VR---V--Q N---KWR--QE | 43 |
| Pax3 | Q-RS--T--A E--EE----A- | ER-H---DIYT -EE---QRAKL | T-AR---V--S N---RWRKQA | 42 |
| Solurshin | Q-RQ--H--S Q--QQ--AT-- | -RN----DMST -EEI-V-TNL | T-AR-RV---K N---KWRKRE | 40 |

PLACENTA TROPHOBLAST-SPECIFIC GENE

BACKGROUND OF THE INVENTION

Several pregnancy termination methods are available in medical or surgical abortion: 1) an 'ordinary abortion' with preoperative ripening of the cervix followed by a vacuum aspiration under heavy sedation; 2) a modified Karman exeresis with a paracervical block; 3) a medical abortion with RU486 and prostaglandin.

Medical termination of pregnancy (medical abortion) as an alternative to surgical abortion has many advantages since it does not require anesthetics and there is no risk of cervical laceration or uterine perforation (Harvey et al. 1995). RU486 (mifepristone) is a best example as an abortifacient medical agent for non-surgical abortion (Cadepond et al. 1997). It is the first steroidal antiprogesterone in clinical use (Cameron et al. 1986; Bygdeman and Van Look 1988). It acts by binding to progesterone receptor, thus blocking the effects of progesterone at the uterine level, and provoking endometrial necrosis and shedding. RU486 can, therefore, be used to interrupt early human pregnancy. In pregnancy of up to 7–8 weeks duration, the rate of completed abortions with RU486 alone has ranged from 50% to 90%. The success rate can, however, be increased up to 95~100% by combining RU486 with a low dose prostaglandin. In addition, possible clinical uses of RU486 include induction of menstruation, late post-coital contraction, induction of labor after intrauterine fetal death, preoperative cervical ripening and treatment of progesterone receptor positive mammary tumors.

Although research has focused on an isolation of abortifacient medical agents that can effectively and safely terminate pregnancy, most of abortifacient medical agents alone do not result in complete abortion. Therefore, a combination of medical agents is commonly used to induce complete abortion (Cameron et al. 1986; el-Refaey and Templeton 1995). An approach to screening large numbers of substances to identify potential abortifacient agents would allow identification of more effective, safe and rapid medical abortion agents that can be used alone or in combination with other agents.

Placenta provides maintenance, nourishment, and protection of the fetus during development and is vital to the survival of the fetus (Cross et al. 1994). Although embryos with organ defects can survive to term, defects in placentation usually results in embryonic death, which reflects the importance of the placenta during embryogenesis. Even seemingly minor defects in placentation can have severe negative consequences. In human, for example, abnormalities in the vascular connections result in preeclampsia, a disease of pregnancy with significant morbidity and mortality to both mother and fetus (Roberts et al. 1993). Such disorders not only affect the health of the mother and fetus, but also represent significant societal costs. Currently, the approaches for the diagnosis and treatment of diseases of pregnancy are limited because of the small number of molecular markers truly specific to the trophoblast cells and our inability to understand their causes.

During mammalian development, the trophoblast is the first lineages to differentiate and gives rise to most of the extraembryonic tissues which are required for implantation and further development of the embryo proper within the uterine environment (Rossant 1986; Cross et al. 1994). It arises from the trophectoderm of the blastocyst and contributes predominantly to the fetal portion of the mature placenta in later development. Human trophoblast in normal implantation and placentation appears to undergo two different pathways of differentiation resulting in the development of villous and extravillous trophoblast (Kurman et al. 1984; Loke and King 1995). Cytotrophoblast (CT) differentiates abruptly into syncytiotrophoblast (ST) on the villous surface as compared with the spectrum of differentiation exhibited by extravillous trophoblast where CT differentiates into intermediate trophoblast (IT) and then into multinucleated intermediate trophoblastic cells (MITC). The various types of gestational trophoblast lesions can be defined and related to discrete pathologic aberrations occurring at different stages of trophoblastic differentiation (Lim et al. 1997; Horn and Bilek 1997; Shin and Kurman 1997).

Therefore, the discovery of trophoblast-specific markers can facilitate the molecular dissection of the lineage and differentiation stages of trophoblast and relate these to various trophoblastic lesions (Mazur and Murman 1994). Furthermore, antibodies against these markers will have considerable value in the study and differential diagnosis of different types of gestational trophoblastic diseases (Losch and Kainz 1996).

The mature murine placenta is composed of three trophoblast layers, namely, the labyrinthine trophoblast, spongiotrophoblast, and giant cell layers, which are each morphologically distinct (Rossant and Croy 1985; Rossant 1995). These specialized murine trophoblast cell types, labyrinthine trophoblast, spongiotrophoblast, and giant cells are homologous to the syncytiotrophoblast, villous cytotrophoblast, and extravillous cytotrophoblast in human placenta, respectively.

We have recently described a novel homeobox-containing gene, Psx, which was isolated from mouse conceptus (Han et al. 1998). It is well known that homeobox genes are involved in controlling cell fates such as body plan during embryo development (De Robertis 1994). Therefore, single mutation can induce major change of the body plan and altered expression of homeobox genes were detected in tumor or malignant transformation. The homeobox genes are characterized by a conserved 180-bp nucleotide sequence known as the homeobox, which encodes a 60-amino acid DNA binding homeodomain structured in three α-helices (Gehring et al. 1994). This DNA binding property indicates that homeodomain proteins function as transcription factors in controlling downstream target genes. In animals, most of these genes have been shown to regulate the coordinated expression of multiple genes involved in development, differentiation and malignant transformation (McGinnis and Krumlauf 1992).

The expression of this gene is first detected at embryonic day 8.5 and limited to the placenta, especially to the trophoblast cell layers of placenta. Therefore, these findings suggest that Psx plays a significant role in the development of placentation, especially in the development of trophoblast specific cell lineages. Accordingly, Psx gene and gene product would be useful as a new trophoblast-specific and stage-specific marker and also in developing therapeutic strategies for the treatment of disorders involving the trophoblast-specific Psx-mediated diseases such as gestational trophoblastic diseases.

SUMMARY OF THE INVENTION

The present invention provides a novel cDNA clone, designated Psx, which encodes a corresponding trophoblast-specific Psx polypeptide including a homeodomain sequence. The expression patterns of Psx can be exploited to detect trophoblast specific lineages such as labyrinthine trophoblast layer and giant cells by the presence of Psx expression. This invention further relates chimeric DNA constructs, vectors and host cells containing the DNA molecules.

Further this invention provides a method to identify putative abortifacient agents, which may be an alternative to surgical abortion. The method involves the steps of: isolating a DNA regulatory region responsive to Psx, stably transforming a heterologous cell line with a first chimeric DNA construct containing a constitutive promoter capable of functioning in the cell line operably linked to a Psx DNA and a second chimeric DNA construct containing the DNA regulatory region operably linked to a reporter gene, and finally culturing the thus-transformed cell line in media containing the compound so that the thus-transformed cell line can be assayed to determine the Psx inhibitory activity of the compound.

This method can be further modified to identify DNA molecules which can inhibit the Psx activity by transiently transfecting the thus-transformed cell line with a third DNA construct containing a constitutive promoter capable of functioning in the cell line operably linked to the DNA molecule, and then culturing the thus-transfected cell line so that it can be assayed to determine the inhibitory activity of the DNA molecule.

Further, this invention relates to Psx polypeptide for generating monoclonal or polyclonal antibodies having specificity for an epitope of Psx polypeptide, and their use in diagnosing trophoblast-specific Psx-mediated diseases such as gestational trophoblastic diseases.

BRIEF DESCRIPTION OF THE DRAWINGS

FIG. 1. Nucleic acid sequence of Psx (SEQ ID NO: 1). The protein sequence is shown below beginning with the initiator methionine at base 44. The homeodomain responsible to DNA binding is underlined from amino acid 150–209.

FIG. 2. Comparison of Psx homeodomain with several known paired-like homeodomains. Shown is a portion of the Psx amino acid sequence set forth in SEQ ID NO. 1 (amino acids 150–209). Dashes indicate positions of amino acid identity between Psx and other sequences. The percentage represents the degree of identity with the amino acid sequence of the Psx homeodomain as a reference. The sources of the sequences are: Mhox (Cserjesi et al. 1992); S8 (Opstelten et al. 1991); Smox-3 (Webster et al. 1992); GSC (Blumberg et al. 1991); Phox2 (Valarche et al. 1993); Shox (Rao et al. 1997); Rx (Mathers et al. 1997); Pax3 (Goulding et al. 1991); Solurshin (Semina et al. 1996).

DETAILED DESCRIPTION OF THE INVENTION

Figure 3A:
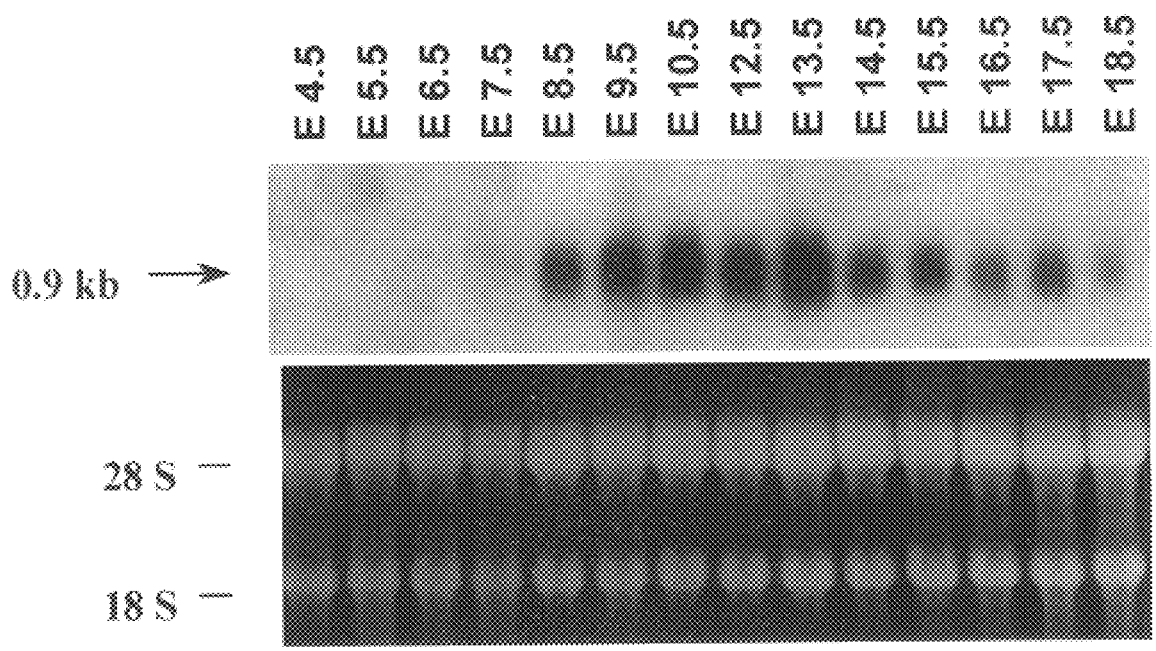
FIGS. 3A and 3B. Northern blot hybridization analysis of Psx mRNA expression patterns during embryo development. Total RNA was prepared from mouse conceptuses including embryos and extraembryonic tissues at the times of gestation indicated (A) or from entire conceptus, fetus, placenta, yolk sac and uterus at 13.5 days of gestation(B). Each lane contained 20 μg of total RNA. The blots were hybridized with $^{32}$P-labeled 5' end Psx cDNA probe as described under Materials and Methods. The control panel (lower part) represents the UV photograph of the gel before blotting, indicating similar levels of 18S and 28S rRNA stained with ethidium bromide. The position of Psx (0.9 kb) is indicated by arrow.

The present applicant has identified a homeobox-containing cDNA clone, referred to Psx. This cDNA was identified by screening a mouse cDNA library prepared from the 13.5 day-old entire conceptus for homeobox-containing sequences using a polymerase chain reaction (PCR) cloning strategy. Northern blot analysis and in situ hybridization experiments showed that the expression of the Psx polynucleotide molecule is first detected at embryonic 8.5 day in extraembryonic tissues, specifically in labyrinthine trophoblast layer and giant cells, both are trophoblast lineages. The expression patterns of Psx can be exploited to detect trophoblast specific lineages such as labyrinthine trophoblast layer and giant cells by the presence of Psx expression. Therefore, a Psx polynucleotide molecule is useful in detection of trophoblast-specific lineages. The detection of the Psx polynucleotide expression in a sample (i.e., tissues or cell lines) indicates that the cells are trophoblast-derived such as labyrinthine trophoblast or giant cells.

Psx expression is detected by hybridization with Psx polynucleotide molecule. The Psx "probe" used to hybridize is a labeled full-length of Psx DNA molecule or preferably a labeled fragment of Psx without the homeobox region in order to avoid cross-hybridization between its homologous homeobox genes. Probes complementary to Psx are prepared by conventional methods, and are preferably allowed to hybridize to mRNA or DNA of samples, using conventional in situ techniques.

In situ techniques which are known in the art may employ the use of fluorescent and radiolabels which can be easily quantitated by fluorescence microscopy or autoradiography, respectively. Another labeling technique may employ enzymatic tags which generate readily quantifiable colorimetric or chemiluminescent signals. The in situ hybridization method to localize the expression of the Psx polynucleotide molecule is described in the Materials and Methods. The intensity of hybridization detected reflects the amount of Psx within the cells of the tissue.

RNA ("Northern") blotting is employed using a Psx polynucleotide molecule of the invention. According to this method, RNA is isolated from tissue by any of a number of standard procedures. RNA is subjected to denaturing gel electrophoresis and transferred to nitrocellulose or other support matrix. The Psx mRNA can be detected by hybridization of radioactively or non-radioactively labeled Psx, or Psx fragments, preferably under high stringency conditions, such as recognized by a scientist in this field. The amount of hybridization can be quantified by densitometric methods.

Further, the polymerase chain reaction ("PCR") is used to detect Psx DNA or mRNA in a sample. To perform PCR, a pair of Psx sequence-specific primers is employed, which hybridize to opposite strands of the Psx gene at offset positions on the double helix. Such primers, taken from the Psx polynucleotide sequences provided in accordance with the invention, represent fragments which preferably are unique to Psx, e.g. sequences having low homology with other proteins than Psx. Two exemplary Psx-specific primer sequences useful in this context include the following sequences (SEQ ID No. 3 and 4), which encode a portion of the intracellular region of Psx:

```
5'- GAA ACT CCT CAA GAC AGC CGC C -3'

5'- CAG CCT ATT CAG AAC ATG TGG GT -3'.
```

Other such primer pairs can be selected and utilized, as well.

The disclosed Psx protein is a homeodomain-containing transcription factor. These proteins have been implicated in transcriptional regulation, development, cell differentiation and malignant transformation (McGinnis and Krumlauf 1992; Gehring et al. 1994). The homeodomains in these proteins are responsible for DNA-binding. The amino acid sequences of mouse Psx protein is shown in FIG. 1 (SEQ ID NO. 2). The homeobox-specific domain includes amino acid residues 150(aa)–209(aa).

A Psx polypeptide, according to the present invention, is produced by recombinant DNA techniques, such as those set forth generally by Maniatis et al., MOLECULAR CLONING-A LABORATORY MANUAL, Cold Spring Harbor Laboratory (1989). Methods specifically suitable to cloning and the Psx polynucleotide molecule are described in the Materials and Methods. The Psx polynucleotide molecule of FIG. 1 (SEQ ID NO. 1) can be cloned into suitable expression vectors and expressed in prokaryotic, insect or eukaryotic expression systems. With conventional techniques, a sequence encoding a Psx protein, can be obtained as a cDNA from mRNA from mouse placenta or mouse placenta cDNA library. The mRNA can be converted to double-stranded DNA using cDNA cloning techniques well-known to the art, including PCR-based techniques. The amplified PCR product of the double-stranded DNA is introduced into a vector, such as a plasmid vector, which has a convenient system for the cloning of PCR products. A suitable plasmid vector in this context is pGEM-T (Promega). Following ligation, by means of standard techniques, the DNA is introduced into a cell, where its expression produces the desired protein. Among prokaryotic hosts, E. coli is preferred. Other prokaryotic hosts such as strains of Bacillus or Pseudomonas may be used, with corresponding control sequences.

Suitable eukaryotic hosts include yeast and mammalian cells. Yeast expression hosts include Saccharomycces, Klebsiella, Picia, and the like. Mammalian cell lines available as hosts for expression are known in the art and include many immortalized cell lines available from the American Type Culture Collection (ATCC), including HeLa cells, Chines hamster ovary (CHO) cells, Choriocarcinoma (BeWo, JAR) cells, and a number of other cell lines. Suitable promoters for mammalian cells are also known in the art and include viral promoters such as that from Simian Virus 40 (SV40), Rous sarcoma virus (RSV), adenovirus (ADV), and bovine papilloma virus (BPV). Mammalian cells may also require terminator sequences and poly-A addition sequences. Enhancer sequences which increase expression may also be included, and sequence which promote amplification of the gene may also be desirable (for example, methotrexate resistance genes). These sequences are known in the art as are suitable vectors. See generally Chapter 16, "Expression of Cloned Genes in Mammalian Cells" in Sambrook et al., Molecular Cloning, A Laboratory Manual, Cold Spring Harbor, N.Y. (1989).

Alternatively, a Psx polypeptide is produced using a commercially available in vitro translation kit from Promega (Madison, Wis.). This kit employs a translation system (including ribosomes, polymerases, amino acids, etc.) derived from rabbit reticulocyte lysates to express Psx mRNA.

Polyclonal and monoclonal antibodies specific to the Psx proteins may be prepared in accordance with standard techniques. Polydonal antibodies, for example, are raised by injecting the protein into an animal, e.g., rabbit to raise anti-Psx antibodies. See, e.g., A. Johnstone and R. Thorpe, Immunochemistry In Practice, Blackwell Scientific Publications, Oxford (1982). Monoclonal antibodies specific to the Psx proteins of the present invention may be prepared according to published method (Choi et al. 1995). This procedure includes the steps of isolating lymphocytes of an animal which has been sensitized or injected with Psx polypeptide, fusing them with myeloma cells to produce hybridomas, then screening the hybridomas for production of "anti-Psx antibodies" which bind preferentially to or exhibit binding specificity for Psx polypeptide. The anti-Psx antibodies of the present invention can be used to detect the cells, such as trophoblast cells, which produce Psx protein.

The antibodies of the present invention may also be used as an aid in the diagnosis of Psx-mediated trophoblast diseases, e.g., gestational trophoblast diseases such as gestational trophoblastic tumors (GTTs), invasive mole (IM), Choriocarcinoma, and placental site trophoblastic tumor (PSTT), in accordance with standard techniques (Shin and Kurman 1997; Fisher et al. 1998). By the term "Psx-mediated", it is meant diseases or conditions mediated by faulty transcriptional or translational aspects of Psx production. In a preferred immunostaining method, a biopsy of an extraembryonic tissue from a patient is obtained, and then stabilized, e.g., fixed in formalin and then embedded in paraffin or other suitable material. The tissue is then sliced. The sliced biopsy preparation is then analyzed for Psx immunoreactivity using a primary anti-Psx antibody, preferably a polyclonal antibody, followed by the addition of a secondary, detectably labeled antibody capable of binding to anti-Psx antibody. A preferred antibody is a goat anti-rabbit IgG, which may be detectably labeled, e.g., with an enzyme such as horseradish peroxidase (HRP). An HRP substrate is added, and the extent of the reaction is indicative of the immunoreactivity of Psx in the sample. Alternatively, the biopsied tissue can be homogenized and then subjected to an immunoassay using a primary antibody which is specific to Psx and a secondary detectably labeled antibody which is capable of binding to anti-Psx antibody. A variety of labels can be used in these methods, including radio-isotopes, enzymes and fluorescent markers. The lack of Psx immunoreactivity may be indicative of such disease.

Gestational trophoblast diseases can be alternatively diagnosed by obtaining a tissue sample from a patient, and isolated DNA therefrom. The gene encoding Psx is isolated, e.g., by using PCR techniques, followed by sequencing the gene. The sequence of the thus-isolated Psx gene is then compared with the nucleic acid sequence of Psx genes isolated from a control group of normal placenta.

The Psx DNA (i.e., DNA molecules encoding proteins having Psx activity) is also used in methods to identify putative therapeutic abortifacient agents, which may offer an alternative to surgery. Applications believe that the expression of Psx in placenta trophoblast is a critical factor in the ultimate differentiation of trophoblast cells, and that in the absence of such expression, trophoblast cells will not undergo complete placentation, e.g., they will be unable to support the full function for the development of embryo during embryogenesis and eventually result in abortion or embryonic death. Psx was localized to the murine X chromosome, which agree with the hypothesis that there are X chromosome-linked genes that specifically regulate the development of extraembryonic tissues (Shao and Takagi 1990). In addition, genomic Southern blot analysis indicated that Psx is a single copy in the mouse genome. These data further support the importance of Psx expression in placenta trophoblast.

To test a non-nucleic acid compound e.g., a hormone, suspected of a having inhibitory activity in accordance with this embodiment of the present invention, a DNA regulatory region (e.g., an enhance or a promoter) responsive to Psx protein is isolated. This is typically done by preparing total genomic DNA, or via PCR techniques. The thus-isolated region is then cloned upstream of a reporter gene, e.g., a luciferase, so that the reporter gene is under the transcriptional control of the cloned regulatory region. The cell line is stably transformed with the thus-prepared construct along with a second chimeric construct containing a constitutive promoter functional in the cell line operably linked to a Psx DNA. A preferred constitutive promoter is a SV40 promoter. The constitutive promoter-Psx gene chimeric construct can be contained in the same vector containing the isolated DNA regulatory region-reporter gene construct, or in a different vector. The thus-transformed cell line is then cultured under suitable conditions in media containing the compound suspected of having Psx inhibitory activity. The inhibitory activity of the compound is determined by the extent of expression of the reporter gene.

To practice this embodiment of present invention with nucleic acid compounds suspected of having Psx inhibitory activity, a stably transformed heterologous cell line described above is transiently transfected with a third chimeric construct containing a constitutive promoter capable of functioning in the cell line operably linked to the nucleic acid of interest. After a suitable incubation period, e.g., about 3–4 days, the cultured cells are assayed for Psx inhibitory activity in the same manner an above.

The present invention is further described with reference to the following, detailed examples. These examples are provided for purposes of illustration only, and are not intended to be limiting unless otherwise specified.

Materials and Methods

Animals and embryo preparation

ICR mice (Dae Han laboratory Animal Research Center, Korea) were used for the isolation of entire conceptuses, embryos and extraembryonic tissues at various stages of development, as well as those of adult tissues. The timed pregnancies were based on the presence of a copulation plug and designated as embryonic day 0.5 (E 0.5), making the assumption that mating had taken place at mid night.

Construction of mouse conceptus cDNA library

Poly(A)$^+$RNA was purified using Oligotex mRNA kit (QIAGEN, Germany) from total RNA extracted from the 13.5-day old mouse conceptus including embryos and extraembryonic tissues according to the manufacturer's procedures. The poly(A)$^+$RNA was converted into double-stranded cDNA using a ZAP Express cDNA synthesis kit (Stratagene, USA). Then, cDNA was ligated with EcoRI- and XhoI-digested ZAP Express vector (Stratagene) and packaged with Gigapack II Gold (Stratagene).

PCR amplification of homeobox-containing cDNA fragments

The mouse conceptus cDNA library was used as a template for the amplification of homeobox sequences by PCR. A degenerate oligonucleotide, 5'-CCA(C/T)TTGGC(C/T)CTTCG(A/G)TT(A/C)(G/T)(A/G)(A/G)AACCA-3' (SEQ ID NO.5), complementary to the sequences encoding the highly conserved homeodomain helix three was designed based on a comparative analysis of paired-like homeodomain DNA sequences selected from GenBank and EMBL databases. It was used as a 3' primer. The universal T3 promoter primer on the ZAP Express vector was used as a 5' primer for the PCR. The amplification reaction contained 10 mM Tris-HCl pH 8.3, 50 mM KCl, 2.5 mM MgCl$_2$, 0.2 mM each dNTP, 1 $\mu$M each primer (Bioneer, Korea), 2.5 units of Taq DNA polymerase (Promega, Madison, USA) and 2 $\mu$l cDNA library suspension containing about 10$^8$ plaque-forming bacteriophage in a final 50 $\mu$l volume. Samples were amplified by two steps of PCR. Primary samples were denatured for 5 min at 94° C. and amplified 35 times, each amplification cycle consisting of 1 min at 94° C., 2 min at 48° C., and 1 min at 72° C. The PCR products were finally extended for 5 min at 72° C. For secondary amplification, 5 $\mu$l of the primary PCR products was used as a template. The secondary amplification was done during 30 cycles, each cycle consisting of 1 min at 94° C., 1 min at 56° C. and 1 min at 72° C. After the last amplification cycle, the PCR products were incubated at 72° C. for 5 min. These PCR products were cloned into the pGEM-T vector (Promega). Inserts of the resulting transformants were sequenced and those containing homeobox sequences were identified using the BLAST family of programs (Benson et al., 1997). The mouse conceptus cDNA library was screened using the PCR-amplified cDNA fragment as a probe.

Isolation of the Psx clone

The mouse conceptus cDNA library (1×10$^6$ plaques) was plated at the density of 5×10$^4$ plaques per plate and screened with the labeled PCR product. The probe was labeled with [$\alpha$-$^{32}$P]dCTP using a random labeling kit (Boehringer, Manheim, Germany). The filters (Hybond-N, Amersham International, Buckinghamshire, UK) were pre-hybridized in buffer containing 6× SSC, 5× Denhardts solution, 0.5% SDS and 0.2 mg/ml denatured salmon sperm DNA for 2 h at 60° C. Hybridization was carried out overnight at 60° C. in the same solution containing the probe. The filters were washed at 60° C. as follows: once at 2× SSC for 30 min; two times for 10 min each at 2× SSC/0.1% SDS; once at 0.1× SSC for 10 min. X-ray films were exposed to the filters between intensifying screens. Positive clones hybridized to the probe were recovered as phagemid plasmids by in vivo excision (ZAP Express cloning kit, Stratagene) according to the manufacturer's protocol.

DNA sequencing analysis

Subcloned PCR products and cDNA clones were sequenced either manually with the Sequenase II kit (Amersham/United States Biochemical) or with an ALFexpress DNA Sequencer (Pharmacia Biotech) using Taq or T7 DNA polymerase and fluorescent carbocyanine dye (Cy5) (Pharmacia Biotech). Computer-assisted sequence analysis was done with the DNASIS program (Hitachi Software, San Bruno, Calif.).

Preparation of RNA and Northern blot analysis

Total RNA was prepared from entire conceptuses, fetus and extraembryonic tissues at various stages of murine development, and from whole pups and adult tissues using either the RNeasy Total RNA Isolation Kit (QIAGEN, Hilden, Germany) or the LiCl/urea method (Hogan et al., 1994). Ten to twenty micrograms of total RNA was denatured in 1× MOPS buffer (20 mM MOPS, 8 mM sodium acetate, 1 mM EDTA), 50% (v/v) deionized formamide and 2.2 M formaldehyde at 65° C. for 15 min and fractionated by electrophoresis on a 1% agarose gel containing 2.2 M formaldehyde and 1× MOPS buffer. The RNA was capillary-blotted in 10× SSC to a Hybond-N membrane. Following prehybridization for at least 2 h in the same prehybridization buffer used for the cDNA library screening at 60° C., the filters were hybridized at 60° C. overnight using fresh QuikHyb buffer (Stratagene). Final washes were at 65° C. as follows: once at 2× SSC for 20 min; three times for 20 min each with 1× SSC/0.1% SDS; once with 0.2× SSC/0.1% SDS for 20 min. The probe DNA was prepared by PCR using the Psx cDNA clone as a template. This cDNA fragment, without the homeodomain sequence, was amplified by using the Psx-specific primers. The PCR product was subcloned into pGEM-T vector (Promega) and verified by sequencing analysis.

In situ hybridization

Pregnant ICR mice were anesthetized intraperitoneally with pentobarbital sodium (50 mg/kg), and the conceptuses were fixed by in vivo perfusion of the heart with 4% paraformaldehyde in phosphate-buffered saline (PBS; containing 137 mM NaCl, 2.7 mM KCl, 4.3 mM $Na_2HPO_4$, and 1.4 mM $KH_2PO_4$) at 4° C. for 10 min. The conceptuses were excised and immersed in the same fixatives for 3 h. The tissues were dehydrated in a graded series of alcohols and then embedded in Paraplast. Tissue sections were cut at 6 m and mounted on gelatine coated slides. The 438 bp N-terminal fragment of Psx cDNA was cloned into the pGEM-T vector. Sense and antisense probes specific for the Psx gene were synthesized using T7 and SP6 RNA polymerases and digoxigenin-11-UTP (Boehringer Mannheim) after linearizing the cDNA clone. The procedures for in situ hybridization histochemistry were performed as previously described (Ahn et al. 1996). Briefly, sections were rehydrated, treated with proteinase K, fixed again, acetylated, dehydrated, and dried. Subsequently, prehybridization solution [50% deionized formamide, 50 mM Tris (hydroxymethyl) aminomethane (Tris) hydrochloride (pH 7.6), 25 mM EDTA (pH 8.0), 20 mM NaCl, 0.25 mg/ml yeast tRNA, and 2.5× Denhardt's solution (100×=0.05% Ficoll, 0.05% polyvinylpyrrolidone, and 0.05% bovine serum albumin)] were applied to the sections, and they were incubated at 5 0° C. for 4 h in a humidified chamber. The slides were then drained and hybridization buffer [50% deionized formamide, 20 mM Tris.HCl (pH 7.6), 1 mM EDTA (pH 8.0), 0.3 M NaCl, 0.5 mg/ml yeast tRNA, 1× Denhardt's solution, and 10% dextran sulfate] containing digoxigenin-11-UTP-labeled sense or antisense cRNA probe was applied. The sections were covered with Parafilm and incubated overnight in a humidified chamber at 50° C. After hybridization, the slides were washed 2× SSC (where 1× SSC is 0.15 M NaCl and 0.015 M sodium citrate, pH 7.0) at room temperature for 30 min, and treated with RNase A (50 ug/ml for 30 min at 37° C.). The sections were washed to a final stringency of 0.1× SSC at 50° C. Hybridization signal was detected with an anti-digoxigenin-alkaline phosphatase conjugate in a colorimetric reaction.

Preparation of genomic DNA and Southern blot analysis

Genomic DNA was prepared from mouse placenta tissues by a modified Blin and Stafford method (Sambrook et al. 1989). Ten micrograms of genomic DNA was digested with XbaI or KpnI and electrophoresed on a 1% agarose gel. The DNA was blotted onto Hybond-N membranes (Amersham) according to the manufacturers instructions. Hybridization was done at 60° C. in QuikHyb solution (Stratagene). After hybridization overnight, the DNA filters were washed as described for the cDNA library screening. To increase the efficiency of the probe in Southern blots, probe DNA was prepared by PCR using mouse genomic DNA as a template. This genomic DNA fragment, which does not contain the homeodomain region, was amplified using Psx-specific primers. PCR amplification and subcloning of the PCR products was done as described for Northern blot analysis.

Fluorescence in Situ Hybridization (FISH) Mapping

Lymphocytes were isolated from male mouse spleen and cultured at 37° C. in RPMI 1640 medium supplemented with 15% fetal calf serum, 3 $\mu$g/ml concanavalin A, 10 $\mu$g/ml lipopolysaccharide and $5 \times 10^{-5}$ M mercaptoethanol. After 44 h., the cultured lymphocytes were treated with 0.18 mg/ml BrdU for an additional 14 h. The synchronized cells were washed and recultured at 37° C. for 4 h in a MEM with thymidime (2.5 $\mu$g/ml). Chromosome slides were made by conventional method as used for human chromosome preparation (hypotonic treatment. Fixation and air dry). The 3.4 kb Psx genomic probe was biotinylated with dATP using the BRL. BioNick labeling kit at 15° C. for 1 h. The procedure for FISH detection was performed according to Heng and Tsui method (1993). Briefly, slides were baked at 55° C. for 1 h. After RNase A treatment, the slides were denatured in 70% formamide in 2× SSC for 2 min at 70° C. followed by dehydration with ethanol. The biotinylated probe was denatured at 75° C. for 5 min in a hybridization solution consisting of 50% formamide and 10% dextran sulfate and mouse cot I DNA and prehybridized for 15 min at 37° C. The probe was loaded on the denatured slides. After an overnight hybridization, the slides were washed and detected as well as amplified using published method (Heng et al. 1992). FISH signals and the assignment of the FISH mapping data with chromosomal bands was achieved by superimposing FISH signals with DAPI bands chromosomes (Heng and Tsui 1993).

Generation and Isolation of Psx protein

Three different bacterial expression plasmids were generated by cloning DNA fragments encoding amino acids 1–247, amino acids 1–149 (N-terminal) and amino acids 150–247 (C-terminal) of the Psx protein into an expression vector pGE-4T1 containing an in-frame glutathionic-S- transferase coding sequence E. coli BL21 culture that had been transformed with these plasmids were grown up. Fusion protein was isolated with glutathione affinity chromatography. In some experiments, the Psx protein was cleaved the glutationic-S-transferase molecule by treatment with thrombin. See generally Chapter 16, "Protein Expression" in Ausubel et al., Current Protocol In Molecular Biology, John Wiley & Sons, Inc. (1997).

Results

Isolation of cDNA clones for Psx

To isolate additional homeobox genes involved in embryo development, the mouse conceptus cDNA library was screened by degenerate PCR. A 0.7 kb PCR product was obtained by PCR-based screening. Nucleotide sequence analysis showed that the 0.7 kb clone contained a novel homeobox sequence. This clone was subsequently used for screening the mouse conceptus cDNA library to obtain full length cDNAs. Four independent clones were obtained. Sequence analysis revealed that all the clones are collinear with different 5 extensions. The largest cDNA clone has a 877 bp insert with a major open reading frame predicted to encode a 247 amino add polypeptide with a molecular mass of 28132 Da (FIG. 1 (SEQ ID No. 1)). The open reading frame is followed by 72 bp of untranslated region terminating in a poly (A) tail. A putative polyadenylation signal sequence (AATAAA) (SEQ ID NO: 6) is present 17 bp upstream from the site of polyadenylation. The deduced amino acid sequence of the protein is predicted to be full-length since the size of the cDNA is close to that of the mRNA calculated from Northern blots.

Sequence analysis

A computer-assisted search of NCBI databases revealed that the deduced amino acid sequence of Psx contains a homeodomain (amino acids 150–209) (FIG. 1 (SEQ ID No. 2)). The Psx homeodomain is divergent compared to other homeodomain sequences. However, the best matches of Psx homeodomain were found to paired-type homeodomain proteins such as Mhox (50%), S8 (48%), Smox-3 (48%), GSC (47%), Phox2 (45%), Shox (45%), Rx (43%), and Solurshin (40%) (FIG. 1B). Homeobox genes within a class usually have greater than 60% identity across the homeodomain (Kappen et al. 1993; Bürglin 1994). Therefore, Psx might be the prototype of a new class of homeobox genes. The Psx homeodomain contains a highly unusual amino acid substitution in one of the four invariant amino acid residues, which are found in all typical homeodomains of higher eukaryotes (Scott et al. 1989). The single substitution is a methionine at position 51 instead of an asparagine. Several atypical homeobox gene proteins such as Pem (Rayle 1991), Cc Aβ1-1, Aβ4-1 (Kües et al. 1992), and Sc Aαz (Stankis et al. 1992) have isoleucine, aspartate, or alanine residue at this homeodomain position. To our knowledge, Psx is the first mammalian homeodomain protein reported to have a methionine at this position. The amino acid at position 51 is known to be involved in direct DNA contact in the paired class homeodomain and other homeodomains (Kissinger et al. 1990; Wilson et al. 1995). The methionine at position 51 deserves further investigation.

The Psx homeodomain also has an arginine at position 50. Most homeodomains have a glutamine at this position, whereas the typical paired class of homeodomains normally possesses a serine residue at this position, characteristic of paired class homeobox genes. Some of the paired-like homeobox genes encode a lysine residue at position 50. Only two Zinc-finger (ZF) class homeobox genes human Atbf1 (Morinaga et al. 1991) and Drosophila zfh-2 (Fortini et al. 1991) have been reported to have an arginine residue at this position. Position 50 has been shown to be critical for conferring different DNA binding specificities to homeodomains (for review see Treisman et al. 1992). The unusual amino acid residues in the conserved positions of the Psx homeodomain may indicate that these amino acids are important for the function of this domain.

Northern blot analysis

Figure 3B:
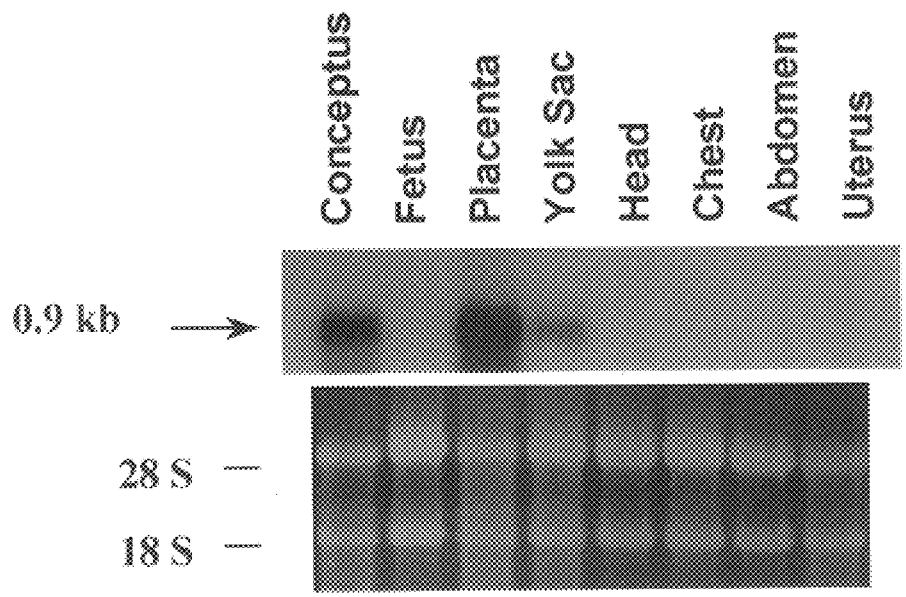

The expression patterns of Psx during embryonic development and in adult tissues were analyzed by Northern blot hybridizations using the Psx-specific cDNA probe without the homeobox region. To determine at which stage of ontogeny the Psx begins to be expressed, total RNA was prepared from entire conceptuses including embryos and extraembryonic tissues from day-4.5 through -18.5 of the 19.5-day mouse gestation period. A transcript of about 0.9 kb was first detected at embryonic day 8.5 and continued to be expressed throughout development (FIG. 3A). The gradual reduction of the expression after 13.5 days was probably correlated with the increasing size of the embryos during development. The embryonic tissue distribution of Psx was examined using embryos and extraembryonic tissues at 13.5 days. The transcript was detected in extraembryonic tissues, mainly in the placenta and with a faint band in the yolk sac but not in the fetus and uterus, suggesting that Psx plays an important role in placenta and yolk sac (FIG. 3B). The entire conceptus including embryos and extraembryonic tissues from day 13.5 was used as a positive control. The signal intensity was stronger in placenta than in the entire conceptus. This is consistent with the fact that the signal was gradually reduced as the size of embryos increased during the development (FIG. 3A).

The placenta and the yolk sac enclose and protect the embryo and provide for the exchange of metabolites with the mother. In particular, placenta prevents attack on the fetus by the maternal immune system and regulates both maternal and fetal physiology through the secretion of hormones (Cross et al. 1994).

Figure 4A:
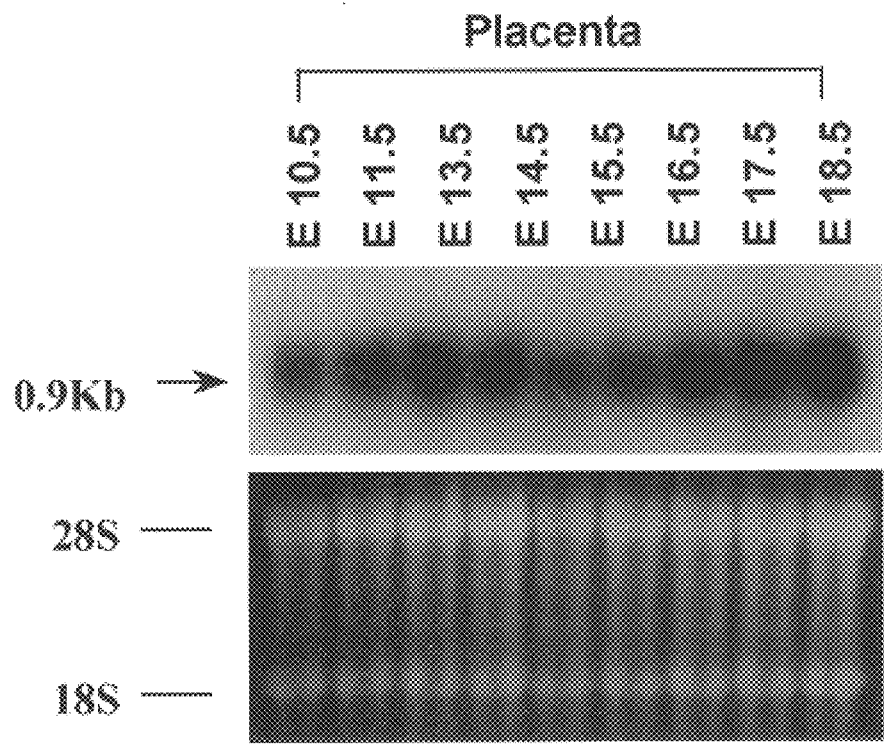
FIGS. 4A and 4B. Northern blot hybridization analysis of Psx mRNA expression in placenta and yolk sac at various stages of development. (A) RNA prepared from placenta at 10.5 days through 18.5 days of 19.5 days gestation period. (B) RNA prepared from yolk sac at 11.5 days through 18.5 days of 19.5 days gestation period. Each lane contained 10 μg of total RNA. Embryonic days are indicated above the lanes. The position of Psx (0.9 kb) is indicated (arrow), as are the positions of the ethidium-stain rRNAs (28S and 18S).
Figure 4B:
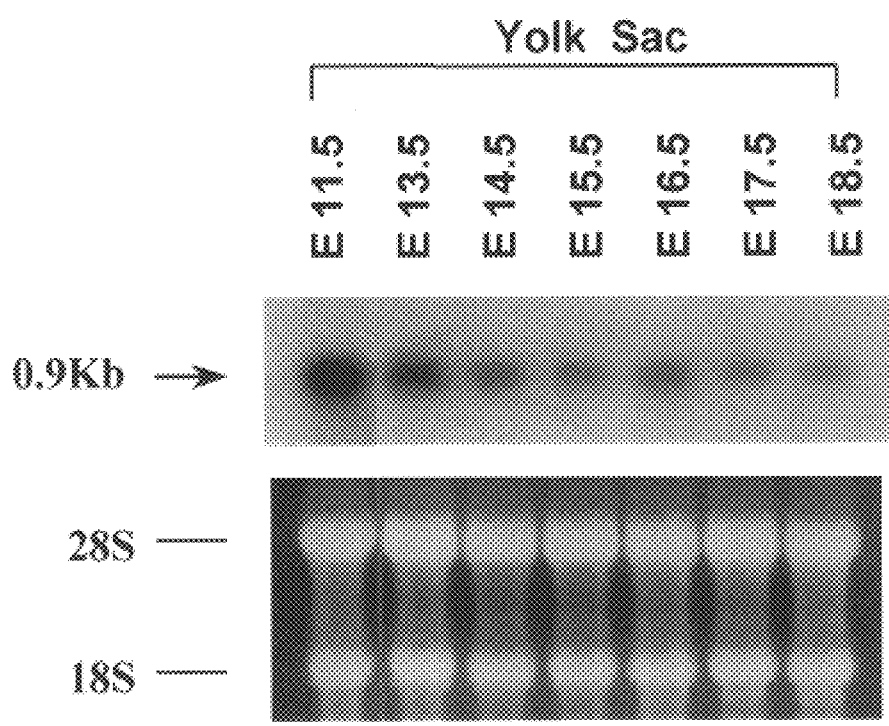

We further examined the expression pattern of Psx in placenta and yolk sac tissues at different stages of the gestation period. The transcript persisted in both tissues during the entire period (FIGS. 4A and 4B). While Psx mRNA was constitutively and highly expressed in placenta (FIG. 4A), it was gradually reduced in yolk sac (FIG. 4B).

Figure 5A:
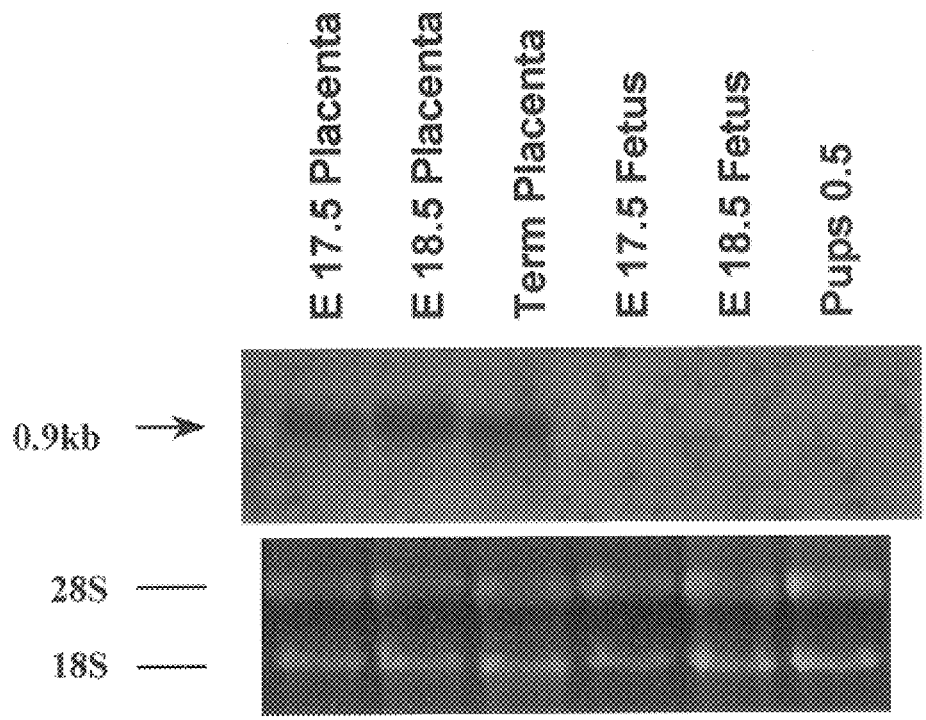
FIGS. 5A and 5B. Northern blot hybridization analysis of Psx mRNA expression in fetus, pup and adult tissues. (A) Total RNA (10 μg) was isolated from placenta and fetus at the times of gestation indicated and from pups at postnatal day 0.5 (p0.5). The day-19.5 placenta was prepared at the time of birth (full term). (B) Total RNA (20 μg) was prepared from various mouse adult organs. The day-18.5 placenta was used as a positive control. The position of Psx (0.9 kb) is indicated by arrow, as are the positions of the ethidium-stained rRNAs (28S and 18S).
Figure 5B:
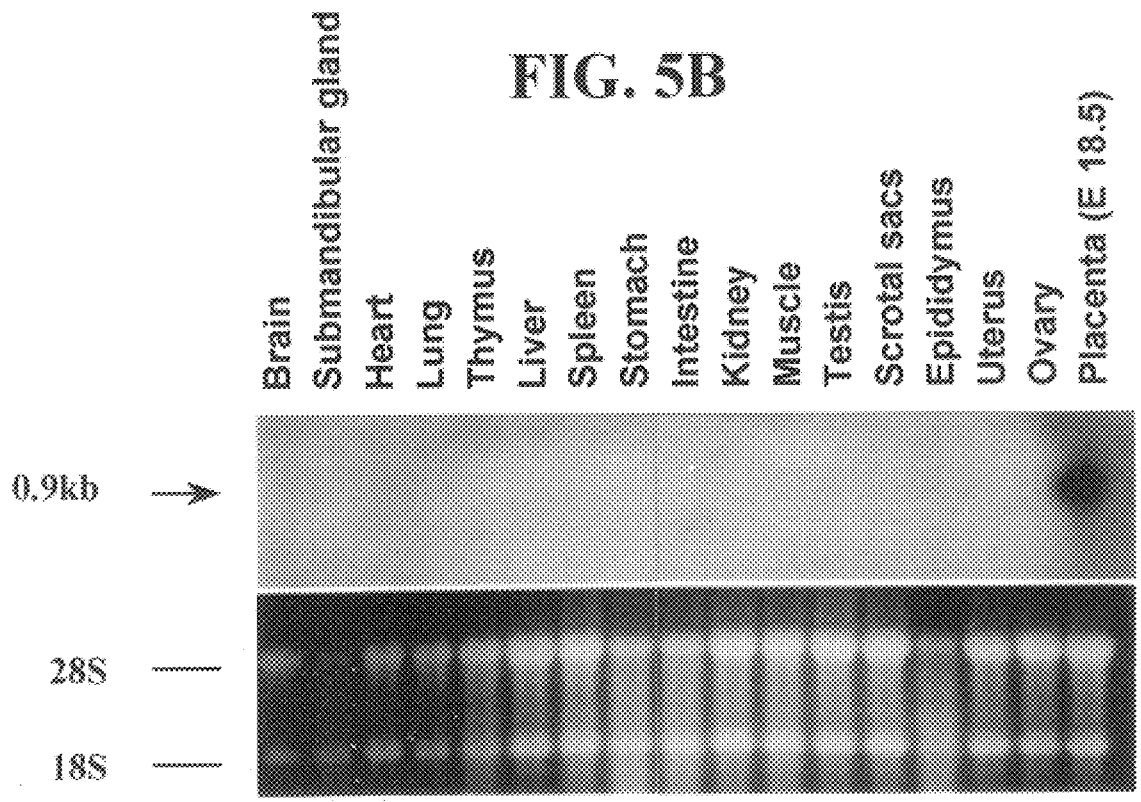

The expression of Psx transcript was also examined in embryos and adult tissues. Psx mRNA was not detected in the fetus at day-17.5 and -18.5, in the new born pups at postnatal day 0.5 (FIG. 5A) and in adult tissues including reproductive organs (FIG. 5B). The adult tissues used were brain, submandibular gland, heart, lung, thymus, liver, spleen, stomach, intestine, kidney, muscle, testis, scrotal sacs, epididymis, uterus, and ovary. The 18.5 day placenta was used as a positive control.

These expression data suggest that Psx plays an important role in the extraembryonic tissues, especially the placenta. Since its expression is highly restricted to extraembryonic tissues, it may be a useful marker for studies of placentation. Psx is a new member of the murine homeobox genes which is expressed in extraembryonic tissues such as placenta and yolk sac but not in any other embryos or adult tissues. A murine homeobox gene Pem, which was previously identified from T-lymphoma cells, was expressed in the placenta and the yolk sac but it also was detected in adult tissues, testis and epididymis (Wilkinson et al. 1990; Maiti et al. 1996). Recently, human homeobox genes HB24, MSX2 and GAX were detected in extraembryonic tissues such as placenta (Quinn et al. 1997). They were originally isolated from T-lymphocytes, ovarian yolk sac tumors, and embryos (Deguchi et al. 1991; Suzuki et al. 1993; Grigoriou et al. 1995, respectively). Both murine MSX2 and the murine homologue of GAX, Mox2, are expressed in the developing spinal cord and limbs and in developing somites and sclerotomal derivatives (Davidson et al. 1991; Günther et al. 1994; Candia et al. 1992). In addition, a novel member of the Distal-less family of homeobox genes, DLX4, has been identified from a human placenta cDNA library (Quinn et al. 1997). However, its expression pattern has not been reported. A key observation reported here for the Psx mRNA is its highly restricted and strong expression in placenta according to the procedures used during the gestation period.

RNA in situ hybridization analysis

Figure 6A:
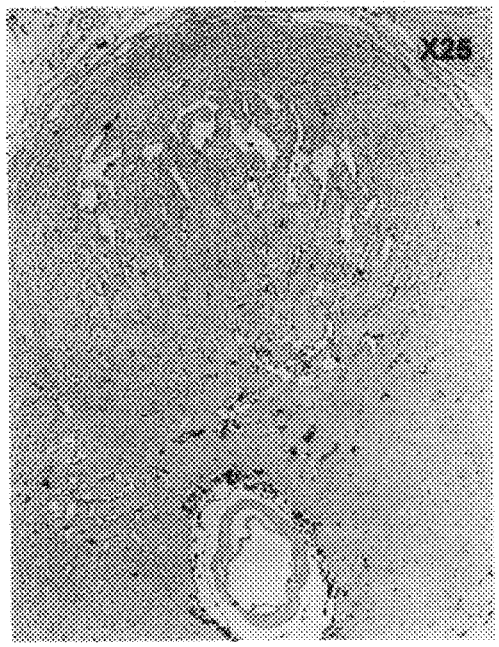
FIGS. 6A–6G. In situ hybridization analysis of Psx mRNA expression with antisense riboprobe. Sagital sections through conceptus within the mouse uterus at E 7.5 (A), E 8.5 (B, C), E 9.5 (D, E), and E 13.5 (F, G), respectively. (C) and (G) are the higher magnification of the boxed area in (B) and (F), respectively. Psx-specific hybridization signals are detected in chorionic ectoderm (Ch), labyrinthine trophoblast (Lb), and giant cells (Gc). No hybridization signals are detected with antisense probe in any of tissues at E 7.5. De: Decidua, Sp: Spongiotrophoblast. Mag. A, B, D, E: X25; F: X50; C: X125; G: X250.
Figure 6B:
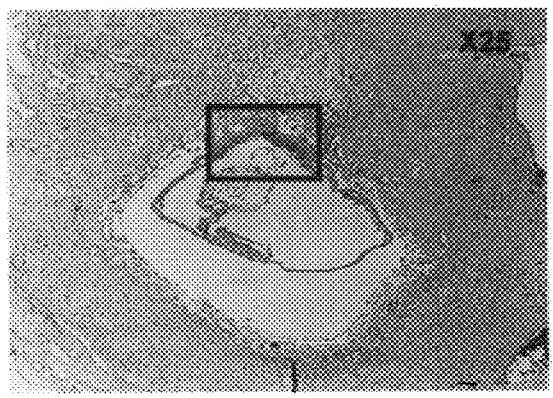
Figure 6C:
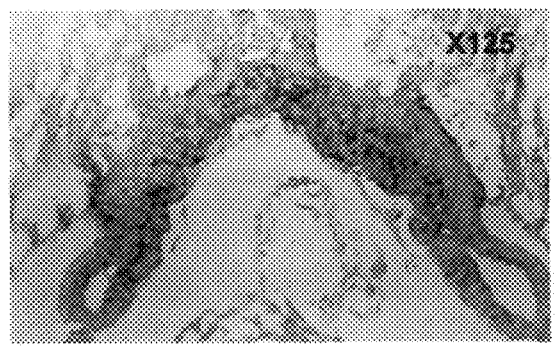
Figure 6D:
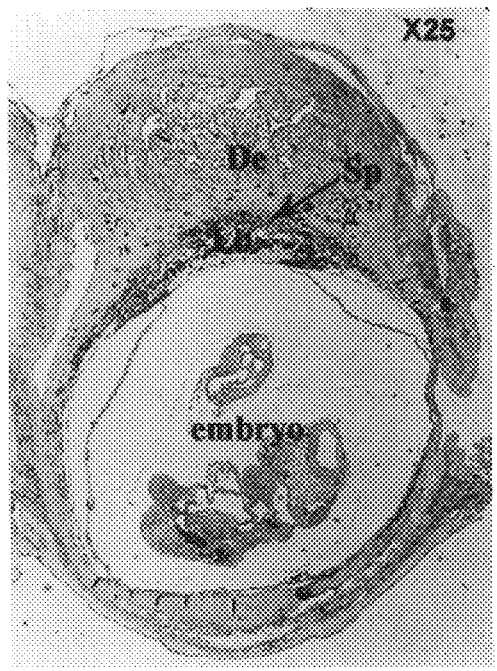
Figure 6E:
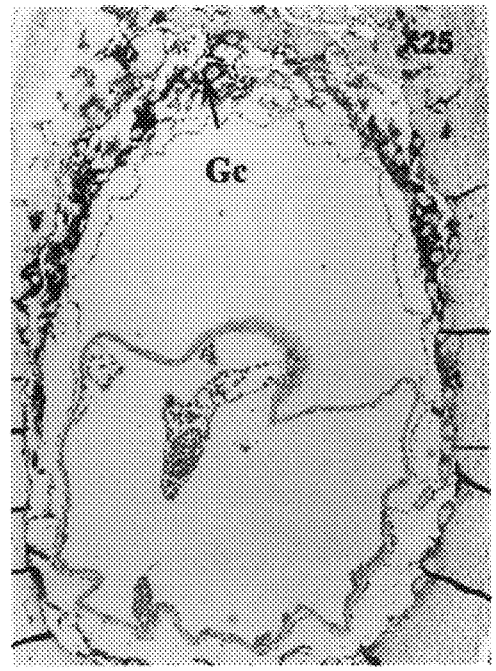
Figure 6F:
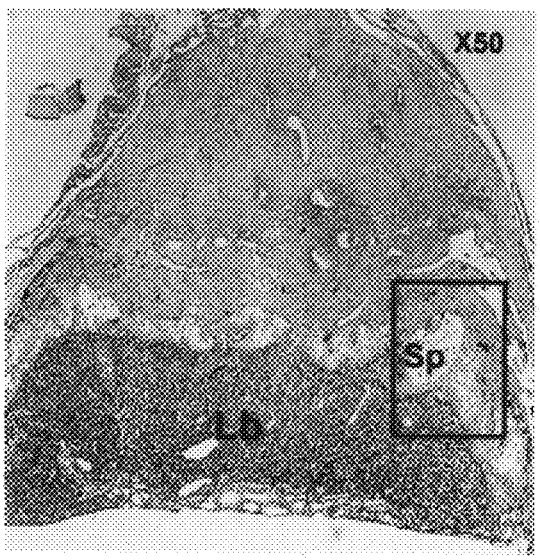
Figure 6G:
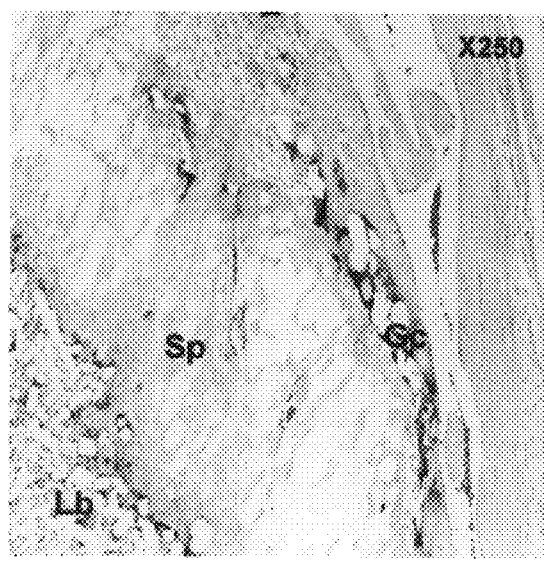

We further examined the localization of the Psx expression in the extraembryonic tissues during embryogenesis by in situ hybridization analysis. Sense and antisense Psx probes were hybridized to 6-μm-thick tissue sections of embryos within the uterus between E 7.0 and E 13.5 (FIG. 6). No specific hybridization signal was observed with the sense probe at any of the stages examined. No hybridization signal was detected with the antisense probe in any of the tissues of the developing embryos (FIG. 6). At E 8.5, Psx transcripts were first detected in the giant cells and chorionic ectoderm (FIG. 6B and 6C). This is consistent with the Northern blot results that the signal was first detected at embryonic day 8.5 (FIG. 3A). At E 9.5 and E 13.5, Psx transcripts were restricted to the giant cells and labyrinthine trophoblast layer (FIGS. 6D–6G). Our data clearly indicate that the chorionic ectoderm is the precorsers of the labyrinthine trophoblast layer. The restricted and constitutive expression of Psx in trophoblast cell layers suggests that Psx plays a critical role in the ultimate differentiation of trophoblast cells, and that in the absence of such expression, trophoblast cells will not undergo complete placentation, e.g., they will be unable to support the full function for the development of embryo during embryogenesis and eventually result in abortion or embryonic death. In addition, Psx will be a useful new molecular marker for the studies of trophoblast-specific lineages. The in situ analysis revealed that the Psx mRNA detection in yolk sac by Northern blot resulted from incomplete dissection and contamination of the yolk sac samples with giant cells.

Southern blot analysis

Figure 7:
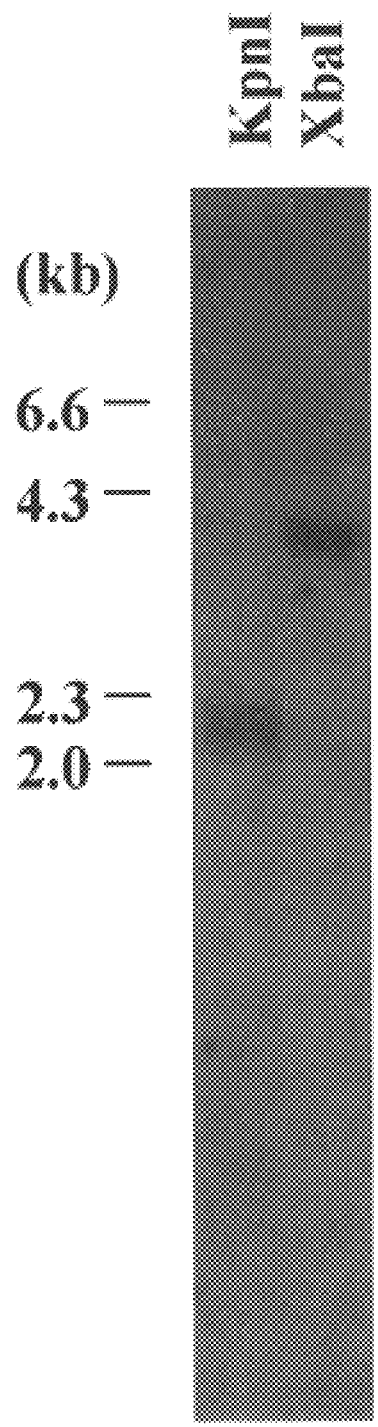
FIG. 7. Southern blot analysis of Psx-related sequences in mouse genomic DNA. Ten μg of genomic DNA isolated from mouse placenta was digested with KpnI and XbaI and hybridized with $^{32}$P-labeled 5' end Psx genomic probe as described under Materials and Methods.

Genomic Southern blots, using a probe DNA that does not contain the homeodomain region to avoid cross-hybridization, indicated that Psx is a single copy in the mouse genome (FIG. 7). The two bands at similar sizes in KpnI-digested DNA are caused by the presence of a KpnI site within the probe DNA, which contains one intron. The presence of the KpnI site within the intron was determined by sequence and restriction enzyme analysis.

Chromosomal assignment

Figure 8A:
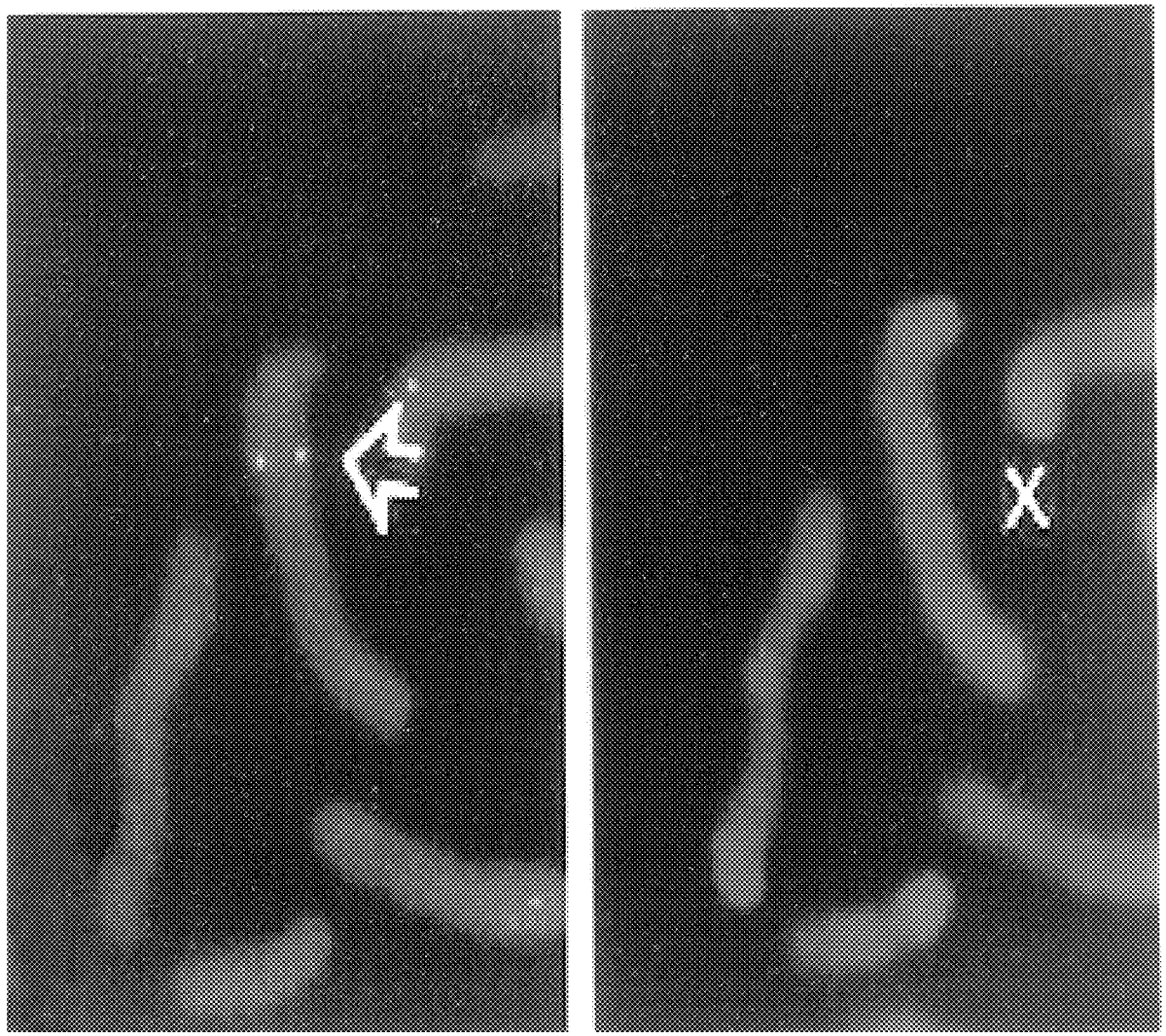
FIGS. 8A and 8B. Chromosomal localization of the mouse Psx gene. (A) Left panel showing the FISH signaling on chromosome; right panel showing the same mitotic figure stained with DAPI to identify chromosome X. (B) Diagram of FISH mapping results for probe Psx. Each dot represents the double FISH signals detected on mouse chromosome X.
Figure 8B:
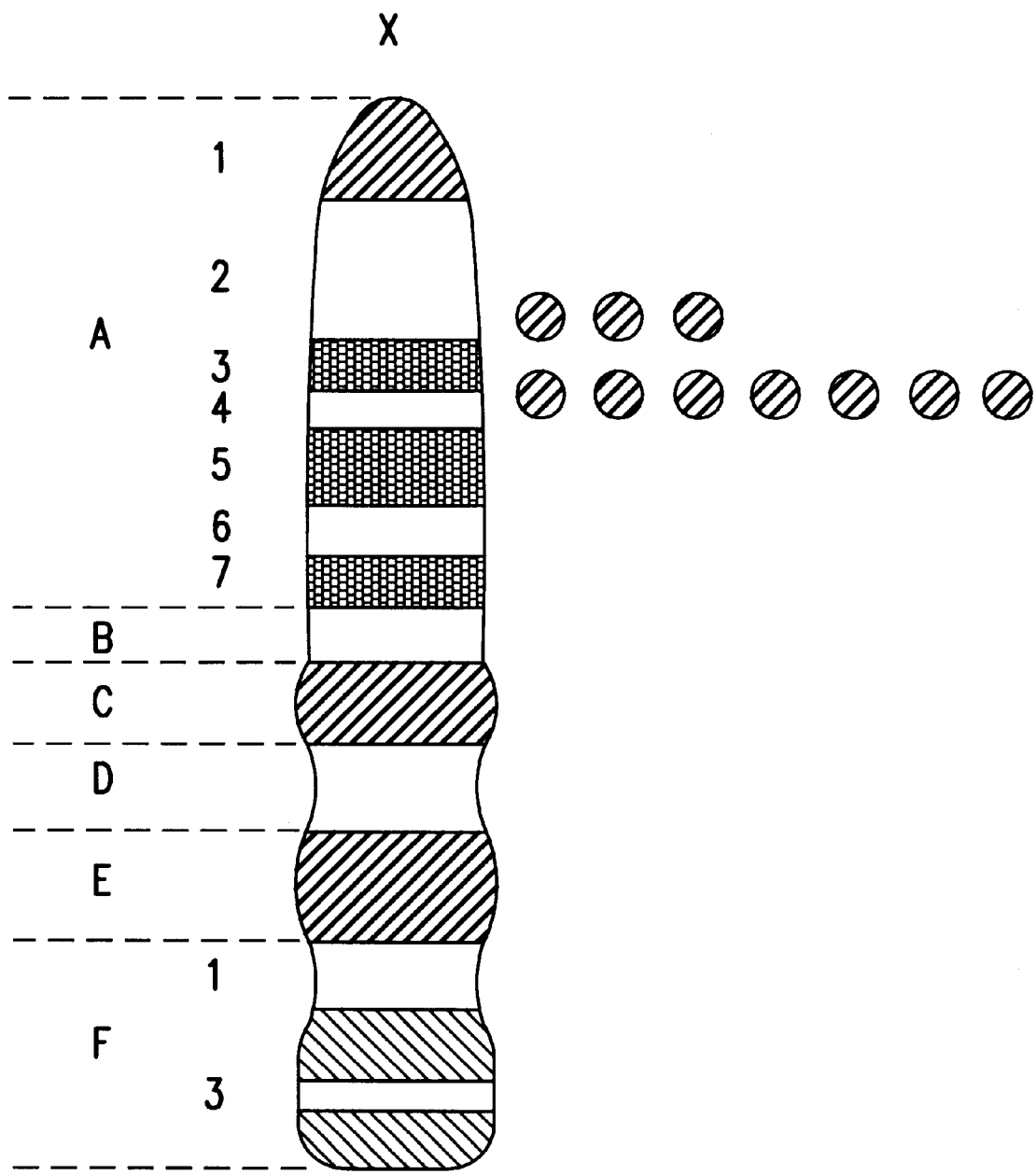

Under the condition used, the hybridization efficiency was 66% for the probe (among 100 checked mitotic figures, 66 of them showed signals on one chromosome). Since the DAPI banding was used to identify the specific chromosome, the assignment between signal from probe and the mouse chromosome X was obtained (FIG. 8A). The detailed position was further determined to region A based on the summary of 10 photos (FIG. 8B). There is no other positive loci detectable under the condition used, therefore, this gene is mapped to chromosome X.

References

Ahn, K. Y., Park, K. Y., Kim, K. K. and Kone, B. C. (1996) Chronic hypokalemia enhances expression of the H+-K+-ATPase α2-subunit gene in renal medulla. Am.J.Physiol. 271: F314–F321

Burgin, T. R. (1994) A comprehensive classification of homeobox genes. In: In: Duboule, D. (ed.), Guidebook to the Homeobox Genes. Oxford University Press, New York, pp. 27–71.

Benson, D. A., Boguski, M. S., Lipman, D. J. and Ostell, J. (1997) GenBank. Nucleic Acids Res. 25: 1–6.

Blumberg, B., Wright, C. V. E., De Robertis, E. M. and Cho, K. W. Y (1991) Organizer-specific homeobox genes in Xenopus laevis embryos. Science 253: 194–196.

Bygdeman, M. and Van Look, P. F. (1988) Anti-progestrones for the interruption of pregnancy. Baillieres. Clin. Obstet Gynaecol. 3: 617–629.

Cadepond, F., Ulmann A, A. and Baulieu, E. E. (1997) RU486(mifepristone): mechanisms of action and clinical uses. Annu.Rev. Med. 48: 129–156.

Cameron, I. T., Michie, A. F. and Baird, D. T. (1986) Therapeutic abortion in early pregnancy with anti-progestogen RU486 alone or in combination with prostaglandin analogue (gemeprost). Contraction 5: 459–468.

Candia, A. F., Hu, J., Crosby, J., Lalley, P. A., Noden, D., Nadeau, J. H. and Wright, C. V. E (1992) Mox-1 and Mox-2 define a novel homeobox gene subfamily and are differentially expressed during early mesodermal patterning in mouse embryos. Development 116: 1123–1136.

Choi, E. Y., Park, S. Y., Jang, S. H., Song, M. S., Cho, S. W. and Choi, S. Y. (1995) Production and characterization of monoclonal antibodies to bovine brain succinic semialdehyde reductase. J. Neurochem. 64: 371–377.

Cross, J. C., Werb, Z., Fisher, S. J. (1994) Implantation and the placenta: key pieces of the development puzzle. Science 266: 1508–1518.

Cserjesi, P., Lilly, B., Bryson, L., Wang, Y., Sassoon, D. A., and Olson, E. M. (1992) Mhox: a mesodermally restricted homeodomain protein that binds an essential site in the muscle creatine kinase enhancer. Development 115: 1087–1101.

Davidson, D. R., Crawley, A., Hill, R. E. and Tickle, C. (1991) Position dependent expression of two related homeodomain genes in developing vertebrate limbs. Nature 352: 429–431.

De Robertis, E. M. (1994) The homeobox in cell differentiation and evolution. In Duboule, D. (ed), Guidebook to the Homeobox Genes, Oxford University Press, New York, pp. 11–23.

Deguchi, Y., Moroney, J. F., Wilson, G. L, Fox, C. H., Winter, H. S. and Kehrl, J. H. (1991) Coning of a human homeobox gene that resembles a diverged Drosophila homeobox gene and is expressed in activated lymphocytes. New Biol. 3; 353–363.

El-Refaey, H. and Templeton, A. (1995) Induction of abortion in the second trimester by a combination of misoprostol and mifepristone: a randomized comparison between two misoprostol regimens. Hum. Reprod. 2: 475–478.

Fisher, R. A. and Newlands, E. S. (1998) Gestational trophoblastic disease: Molecular and genetic studies. J. Reprod. Med. 43: 87–97.

Fortini, M. E., Lai, Z. and Rubin, G. M. (1991) The Drosophila zfh-1 and zfh-2 genes encode novel proteins containing both zinc-finger and homeodomain motifs. Mech Dev. 34: 113–122.

Günther, T., Struwe, M., Aguzzi, A. and Schughart, K (1994) Open brain, a new mouse mutant with severe neural tube defects, shows altered expression in the developing spinal chord. Development 120: 3119–3130.

Gehring, W. J., Affolter, M. and Bürglin, T. (1994) Homeodomain proteins. Annu. Rev. Biochem. 63: 487–526.

Goulding, M., Chalepakis, G., Deutsch, U., Ersclius, J. and Gruss, P. (1991) Pax-3, a novel murine DNA binding protein expressed during early neurogenesis. EMBO J. 10: 1135–1147.

Han, Y. J., Park, A. R., Sung, D. Y. and Chun, J. Y. (1998) Psx, a novel murine homeobox gene expressed in placenta. Gene 207: 159–166.

Harvey, S. M., Beckman, L. J., Castle, M. A. and Coeytaux, F. (1995) Knowledge and perceptions of medical abortion among potential users. Fa,. Plann. Perspect. 5: 203–207.

Heng, H. H. Q., Squire, J. and Tsui, L. C. (1992) High resolution mapping of mammalian genes by in situ hybridization to free chromatin. Proc. Natl. Acad. Sci. USA. 89: 9509–9513.

Heng, H. H. Q. and Tsui, L. C. (1993) Modes of DAPI banding and simultaneous in situ hybridization. Chromosoma 102: 325–332.

Hogan, B., Beddington, R., Costantini, F. and Lacy, E. (1994) Manipulating the Mouse Embryo: A Laboratory Manual. Cold Spring Harbor Laboratory Press, Cold Spring Harbor, N.Y.

Horn, L. C. and Bilek, K. (1997) Histologic classification and staging gestational trophoblastic disease. Gen Diagn Pathol 143: 87–101.

Kües, U., Richardson, W. V. J., Tymon, A. M., Mutasa, E. S., Güttgens, B., Gaubatz, S., Gregoriades, A. and Casselton, L. A. (1992) The combination of dissimilar alleles of the Aa and Ab gene complexes, whose proteins contain homeodomain motifs, determines sexual development in the mushroom *Coprinus cinereus*. Genes Dev. 6: 568–577.

Kappen, C., Schughart, K and Ruddle, F. H. (1993) Early evolution origin of major homeodomain sequence classes. Genomics 8: 54–70.

Kissinger, C. R., Liu, B., Martin-Blanco, E., Kornberg, T. B. and Pabo, C. O. (1990) Crystal structure of an engrailed homeodomain-DNA complex at 28 $3_F$ resolution: a framework for understanding homeodomain-DNA interactions. Cell 63: 579–590.

Kurman, R. J., Main, C. S. and Chen, M. C. (1984) A distinctive form of trophoblast with specific morphological, biological and functional features. Placenta 5: 349–355.

Lim, K. H., Zhou, Y., Janatpour, M., McMaster, M., Bass, K., Chun, S. H. and Fisher, S. J. (1997) Human cytotrophoblast differentiationinvasion is abnormal in pre-eclampsia. Am J Pathol 151: 1809–1818.

Loke, Y. W. and King, A. (1991) Human trophoblast development. In Human implantation-cell biology and immunology. First edition 1995, Cambridge University Press, pp32–62.

Losch, A and Kainz, C. (1996) Immunohistochemistry in the diagnosis of the gestational trophoblastic disease. Acta Obstet Gynecol Scand 75: 753–756.

Maiti, S., Doskow, J., Sutton, K., Nhim, R. P., Lawlor, D. A., Levan, K, Lindsey, J. S. and Wilkinson, M. F. (1996) The Pem homeobox gene: rapid evolution of the homeodomain, X chromosomal localization, and expression in reproductive tissue. Genomics 34: 304–316.

Mathers, P. H., Grinberg, A., Mahon, K. A. and Jamrich, M. (1997) The Rx homeobox gene is essential for vertebrate eye development. Nature 387: 603–607.

Mazur, M. T. and Murman, R. J. (1994) Gestational trophoblastic disease and related lesions. In: Kurman R J, ed. Blausteins pathology of the female genital tract. New York: Springer, pp 1049–1093.

McGinnis, W. and Krumlauf, R. (1992) Homeobox genes and axial patterning. Cell 68: 283–302.

Morinaga, T., Yasuda, H., Hashimoto, T., Higashio, K. and Tamaoki, T. (1991) A human-fetoprotein enhancer-binding protein, ATBF1, contains four homeodomains and seventeen zinc fingers. Mol. Cell. Biol. 11: 6041–6049.

Opstelten, D. J., Vogels, R., Robert, B., Kalkhoven, E., Zwartkruis, F., de Laaf, L., Destree, O. H., Deschamps, J., Lawson, K. A. and Meijlink, F. (1991) The mouse homeobox gene, S8, is expressed during embryogenesis predominantly in mesenchyme. Mech. Dev. 34: 29–41.

Quinn, L. M., Johnson, B. V., Nicholl, J., Sutherland, G. R. and Kalionis, B. (1997) Isolation and identification of homeobox genes from the human placenta including a novel member of the Distal-less family, DLX4. Gene 187: 55–61.

Rao, E., Weiss, B., Fukami, M., Rump, A., Niesler, B., Mertz, A., Muroya, K, Binder, G., Kirsch, S., Winkelmann, M., Nordsiek, G., Heinrich, U., Breuning, M. H., Ranke, M. B., Rosenthal, A., Ogata, T. and Rappold, G. A. (1997) Pseudoautosomal deletions encompassing a novel homeobox gene cause growth failure in idiopathic short stature and Turner syndrome. Nature Genet. 16: 54–63.

Rayle, R. E. (1991) The oncofetal gene Pem specifies a divergent paired class homeodomain. Dev. Biol. 146: 255–257.

Roberts, J. M., Taylor R. N., Friedman, S. A. and Goldfien A. (1993) in Fetal Medical Review, W. Dunlop, Ed. Arnold, London.

Rossant, J. (1986) Development of extraembryonic cell lineages in the mouse. In Experimental Approaches to Mammalian Embryonic Development (J. Rossant and R. A. Pederson, Ed.), pp. 97–120. Cambridge Univ. Press, London.

Rossant, J. (1995) Development of the extraembryonic lineages. Semi. Dev. 6: 237–247.

Rossant, J. and Croy, B. A. (1985) Genetic identification of tissue of origin of cellular population within the mouse placenta. J. Embryol. Exp. Morphol. 86: 177–189.

Sambrook, J., Fritsch, E. F. and Maniatis, T. (1989) Molecular Cloning: A Laboratory Manual. Cold Spring Harbor Laboratory Press, Cold Spring Harbor, New York.

Scott, M. P., Tamkun, J. W. and Hartzell III, G. W. (1989) The structure and function of the homeodomain. Biochim. Biophys. Acta. Rev. Cancer. 989: 25–48.

Semina, E. V., Reiter, R., Leysens, N. J., Alward, W. L. M., Small, K. W., Datson, N. A., Siegel-Bartelt, J., Bierke-Nelson, D., Bitoun, P., Zabel, B. U., Carey, J. C. and Murray, J. C. (1996) Cloning and characterization of a novel bicoid-related homeobox transcription factor gene, RIEG, involved in Rieger syndrome. Nature Genet. 14: 392–399.

Shao, C. and Takagi, N. (1990) Anextra maternally derived X chromosome is deleterious to early mouse development. Development 110: 969–975.

Shin, I. M. and Kurman, R. J. (1997) New concepts in trophoblastic growth and differentiation with practical application for the diagnosis of gestational trophoblastic disease. Verh Dtsch Ges Pathol 81: 266–272.

Stankis, M. M., Specht, C. A., Yang, H., Giasson, L., Ullrich, R. C. and Novotny, C. P. (1992) The Aα mating locus of *Schizophyllum commune* encodes two dissimilar, multiallelic, homeodomain proteins. Proc. Natl. Acad. Sci. USA 89, 7169–7173.

Treisman, J., Harris, E, Wilson, D., and Desplan, C. (1992) The homeodomain: a new face for the helix-turn-helix? Bioessays 14: 145–150.

Valarche, I., Tissier-Seta, J. P., Hirsch, M. R., Martinez, S., Goridis, C. and Brunet, J. F. (1993) The mouse homeodomain protein Phox2 regulates Ncam promoter activity in concert with Cux/CDP and is a putative determinant of neurotransmitter phenotype. Development 119: 881–896.

Webster, P. J. and Mansour, T. E. (1992) Conserved classes of homeodomains in *Schistosoma mansoni,* an early bilateral metazoan. Mech. Dev. 38: 25–32.

Wilkinson, M. F., Kleeman, J., Richards, J. and MacLeod, C. L. (1990) A novel oncofetal gene is expressed in a stage-specific manner in murine embryonic development. Dev. Biol. 141: 451–455.

Wilson, D. S., Guenther, B., Desplan, C. and Kuriyan, J. (1995) High resolution crystal structure of a paired (Pax) class cooperative homeodomain dimer on DNA. Cell 82: 709–719.

What is claimed is:

1. An isolated nucleic acid molecule encoding a placenta-specific homeobox protein (Psx) having amino acid sequence SEQ ID NO. 2.

2. The isolated nucleic acid molecule of claim 1, wherein the nucleic acid molecule is a messenger RNA molecule.

3. The isolated nucleic acid molecule of claim 1, wherein the nucleic acid molecule is a DNA molecule.

4. The isolated nucleic acid molecule of claim 3, wherein the DNA molecule is a cDNA molecule.

5. The cDNA molecule of claim 4 having a nucleotide sequence shown in FIG. 1 (SEQ ID No. 1).

6. The cDNA molecule of claim 5, wherein a detectable marker is labelled with the cDNA molecule.

* * * * *

SEQUENCE LISTING

```
<160> NUMBER OF SEQ ID NOS: 6

<210> SEQ ID NO 1
<211> LENGTH: 877
<212> TYPE: DNA
<213> ORGANISM: mouse

<400> SEQUENCE: 1
ggaagcctct tcgggagcag cgtcggatcc agagattctc gctatggaaa ctcctcaaga     60
cagccgccaa agcatccaaa agcctccgag tccggcagcc gaggaggaca aggaagaaca    120
gcctggtggg aatgcagtgg tctccggggc tccagaggaa agaatagaca agaaagagct    180
tgtactgaac tggctcgctc agggtgagtt tgatcagggc gaaggcctca gggcgaggtt    240
gctggaggtg agcaggctca agaagagcct gtccattgag tccagctcag gaagccactg    300
gaggagaaga ggagggagaa aaaaggaagg agaaatggaa ggaagacatg ctggtgatgg    360
tgcttctagc tccgaggatg acagcatcct ggaagaaggc ggccaaaaca tagatcaaca    420
gccgcctcag caagaggcag ccagtcctga tagcatcaga aacccacatg ttctgaatag    480
gctggctcaa ctgcggtaca gacgcaccag gttcacccac tctcagctgc atgacctgga    540
gcgccttttc caagagactc gctacccag cttgcgagca aggagggatc ttgcacgatg    600
gatgggtgtg gatgaatgtg atgtgcagaa ttggtttcgg atgaggagag ccctttccca    660
gagaaacagg agagtgctga tgttctgcga actgccgcct cttccccaga gcgactctcc    720
tgaagatttt ggagcagact tgagtgccag ccctgtcatg gagccagatg aggatggctt    780
cttctgagcc acccatgatg gccatgacaa ccttttcttc tctacaatta tttcagcaat    840
aaagatgagc attctgaata aaaaaaaaa aaaaaaa                              877

<210> SEQ ID NO 2
<211> LENGTH: 247
<212> TYPE: PRT
<213> ORGANISM: mouse

<400> SEQUENCE: 2

Met Glu Thr Pro Gln Asp Ser Arg Gln Ser Ile Gln Lys Pro Pro Ser
  1               5                  10                  15

Pro Ala Ala Glu Glu Asp Lys Glu Glu Gln Pro Gly Gly Asn Ala Val
                 20                  25                  30

Val Ser Gly Ala Pro Glu Glu Arg Ile Asp Lys Lys Glu Leu Val Leu
             35                  40                  45

Asn Trp Leu Ala Gln Gly Glu Phe Asp Gln Gly Glu Gly Leu Arg Ala
         50                  55                  60

Arg Leu Leu Glu Val Ser Arg Leu Lys Lys Ser Leu Ser Ile Glu Ser
 65                  70                  75                  80

Ser Ser Gly Ser His Trp Arg Arg Gly Arg Lys Lys Glu Gly
                 85                  90                  95
```

```
Glu Met Glu Gly Arg His Ala Gly Asp Gly Ala Ser Ser Ser Glu Asp
             100                 105                 110

Asp Ser Ile Leu Glu Glu Gly Gly Gln Asn Ile Asp Gln Gln Pro Pro
             115                 120                 125

Gln Gln Glu Ala Ala Ser Pro Asp Ser Ile Arg Asn Pro His Val Leu
130                 135                 140

Asn Arg Leu Ala Gln Leu Arg Tyr Arg Arg Thr Arg Phe Thr His Ser
145                 150                 155                 160

Gln Leu His Asp Leu Glu Arg Leu Phe Gln Glu Thr Arg Tyr Pro Ser
                165                 170                 175

Leu Arg Ala Arg Arg Asp Leu Ala Arg Trp Met Gly Val Asp Glu Cys
                180                 185                 190

Asp Val Gln Asn Trp Phe Arg Met Arg Arg Ala Leu Phe Gln Arg Asn
                195                 200                 205

Arg Arg Val Leu Met Phe Cys Glu Leu Pro Pro Leu Pro Gln Ser Asp
            210                 215                 220

Ser Pro Glu Asp Phe Gly Ala Asp Leu Ser Ala Ser Pro Val Met Glu
225                 230                 235                 240

Pro Asp Glu Asp Gly Phe Phe
                245
```

```
<210> SEQ ID NO 3
<211> LENGTH: 22
<212> TYPE: DNA
<213> ORGANISM: mouse

<400> SEQUENCE: 3
gaaactcctc aagacagccg cc                                          22

<210> SEQ ID NO 4
<211> LENGTH: 23
<212> TYPE: DNA
<213> ORGANISM: mouse

<400> SEQUENCE: 4
cagcctattc agaacatgtg ggt                                         23

<210> SEQ ID NO 5
<211> LENGTH: 27
<212> TYPE: DNA
<213> ORGANISM: mouse
<220> FEATURE:
<221> NAME/KEY: allele
<222> LOCATION: (4)
<223> OTHER INFORMATION: y at position 4 is c or t
<220> FEATURE:
<221> NAME/KEY: allele
<222> LOCATION: (10)
<223> OTHER INFORMATION: y at position 10 is c or t
<220> FEATURE:
<221> NAME/KEY: allele
<222> LOCATION: (16)
<223> OTHER INFORMATION: r at position 16 is a or g
<220> FEATURE:
<221> NAME/KEY: allele
<222> LOCATION: (19)
<223> OTHER INFORMATION: m at position 19 is a or c
<220> FEATURE:
<221> NAME/KEY: allele
<222> LOCATION: (20)
<223> OTHER INFORMATION: k at position 20 is g or t
<220> FEATURE:
<221> NAME/KEY: allele
<222> LOCATION: (21)
<223> OTHER INFORMATION: r at position 21 is a or g
```

```
<220> FEATURE:
<221> NAME/KEY: allele
<222> LOCATION: (22)
<223> OTHER INFORMATION: r at position 22 is a or g

<400> SEQUENCE: 5
ccayttggcy cttcgrttmk rraacca                                               27

<210> SEQ ID NO 6
<211> LENGTH: 6
<212> TYPE: DNA
<213> ORGANISM: mouse

<400> SEQUENCE: 6 aataaa                                                                       6
```